(12) United States Patent
Kimmel et al.

(10) Patent No.: US 9,533,120 B1
(45) Date of Patent: Jan. 3, 2017

(54) TRANSSEPTAL NEEDLE ASSEMBLY

(71) Applicant: Greatbatch Ltd., Clarence, NY (US)

(72) Inventors: Scott Kimmel, St. Paul, MN (US);
Kevin Pietsch, Greenfield, MN (US);
Mark Nelson, Plymouth, MN (US);
Gregory A. Boeshans, Blaine, MN (US); Jason M. Romanowski,
Richfield, MN (US)

(73) Assignee: Greatbatch Ltd., Clarence, NY (US)

( * ) Notice: Subject to any disclaimer, the term of this patent is extended or adjusted under 35 U.S.C. 154(b) by 924 days.

(21) Appl. No.: 13/692,759

(22) Filed: Dec. 3, 2012

Related U.S. Application Data

(60) Provisional application No. 61/566,203, filed on Dec. 2, 2011.

(51) Int. Cl.
*A61M 25/01* (2006.01)

(52) U.S. Cl.
CPC .................. *A61M 25/0102* (2013.01)

(58) Field of Classification Search
CPC ................ A61B 2017/00243; A61B 17/0057;
A61B 2017/00247; A61B
2017/00575; A61B 17/00234; A61B
2017/0046; A61M 25/0068
See application file for complete search history.

(56) References Cited

U.S. PATENT DOCUMENTS

| | | | |
|---|---|---|---|
| 4,790,825 A * | 12/1988 | Bernstein et al. | 604/170.02 |
| 5,098,392 A | 3/1992 | Fleischhacker et al. | |
| 5,190,528 A | 3/1993 | Fonger et al. | |
| 5,312,363 A * | 5/1994 | Ryan et al. | 604/167.04 |
| 5,630,830 A | 5/1997 | Verbeek | |
| 5,766,151 A * | 6/1998 | Valley et al. | 604/103.07 |
| 7,001,396 B2 * | 2/2006 | Glazier et al. | 606/108 |
| 7,922,696 B2 | 4/2011 | Tal et al. | |
| 7,963,947 B2 | 6/2011 | Kurth et al. | |
| 2004/0186346 A1 * | 9/2004 | Smith et al. | 600/102 |
| 2005/0149049 A1 * | 7/2005 | Assell et al. | 606/99 |
| 2005/0154389 A1 * | 7/2005 | Selover et al. | 606/61 |
| 2007/0270751 A1 | 11/2007 | Stangenes | |
| 2008/0045861 A1 * | 2/2008 | Miller et al. | 600/567 |
| 2008/0262430 A1 * | 10/2008 | Anderson et al. | 604/164.1 |
| 2008/0294111 A1 * | 11/2008 | Tal et al. | 604/165.01 |
| 2009/0194446 A1 * | 8/2009 | Miller et al. | 206/438 |
| 2010/0249491 A1 | 9/2010 | Farnan et al. | |
| 2010/0331900 A1 * | 12/2010 | Garabedian et al. | 606/86 A |
| 2012/0143206 A1 * | 6/2012 | Wallace et al. | 606/103 |
| 2013/0304051 A1 * | 11/2013 | Kimmel et al. | 606/33 |

* cited by examiner

*Primary Examiner* — Scott Medway

(74) *Attorney, Agent, or Firm* — Steven W. Winn; Michael F. Scalise

(57) ABSTRACT

A transseptal needle assembly comprised of a cannula, a handle assembly and a stylet is described. The cannula of the needle assembly is of a uniform body construction such that the cannula main portion and needle portion are fluidly connected in one-piece. The handle assembly comprises a handle housing, a handle sleeve and a handle slug. The handle slug provides ballast which improves tactile feel of the needle assembly. In addition, the stylet comprises a stylet housing having a hinged designed that allows for easier control of the stylet.

28 Claims, 6 Drawing Sheets

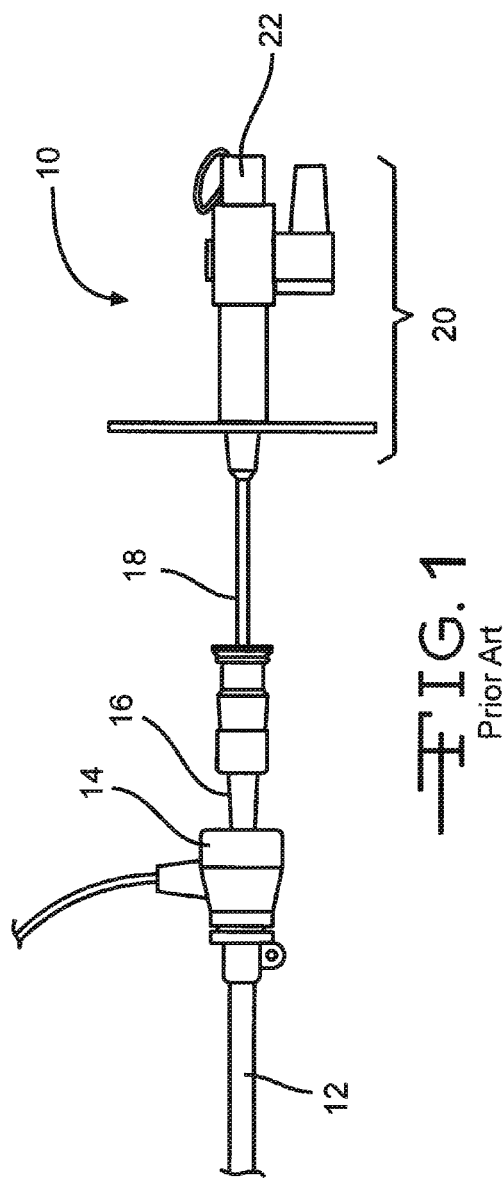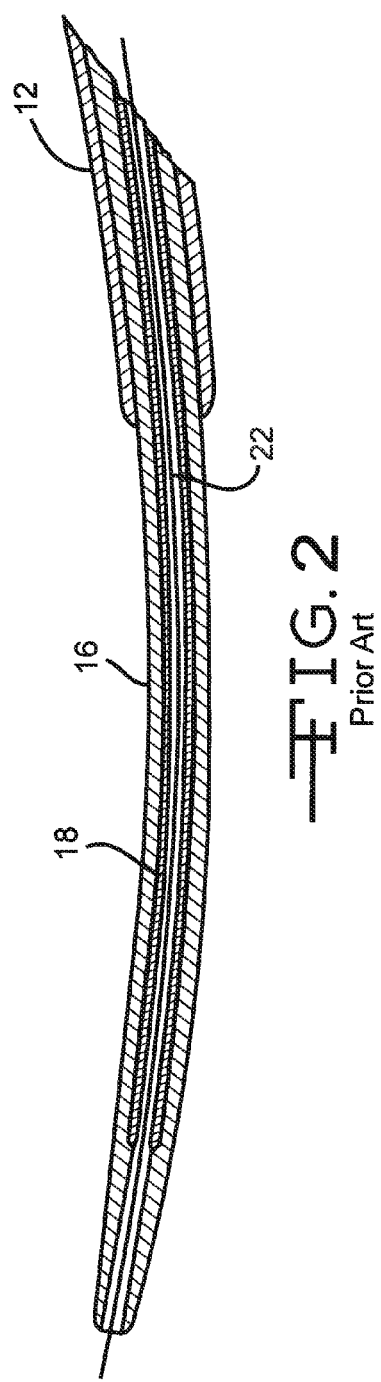
FIG. 1
Prior Art
FIG. 2
Prior Art

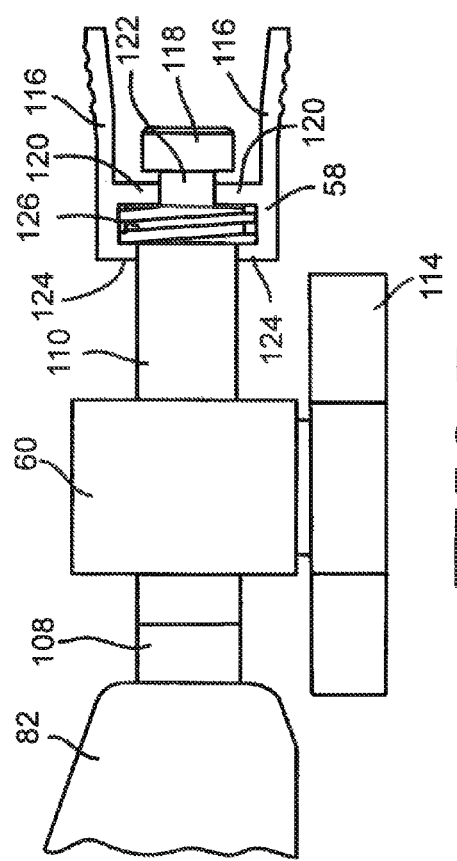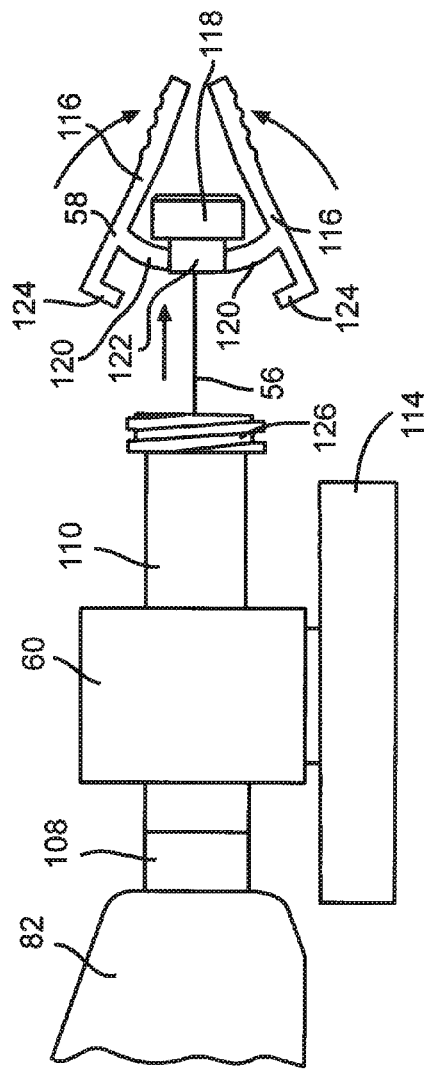

TRANSSEPTAL NEEDLE ASSEMBLY

CROSS-REFERENCE TO RELATED APPLICATION

This application claims priority from U.S. Provisional Patent Application Ser. No. 61/566,203, filed Dec. 2, 2011.

FIELD OF THE INVENTION

The present invention relates to the art of transvenous catheters, and more particularly, to a transseptal needle assembly used to gain access to the internal chambers of the heart.

PRIOR ART

A catheter device is commonly used to facilitate and perform many therapeutic and diagnostic cardiovascular procedures. In general, a catheter is introduced into the vasculature and advanced into position within the body. Such catheters are also often used to gain access within the human heart. However, the complex structure and tortuous paths within the human vasculature and heart make the use of a catheter difficult. Prior art catheters, particularly transseptal needle catheters, are generally constructed having separate movable sheath and dilator assemblies. These prior art catheter devices generally operate by coordinating the position of sheath and dilator assemblies over a guide wire.

The human heart contains four chambers, the right atrium, the right ventricle, the left atrium and the left ventricle. The right atrium is separated from the right ventricle by the tricuspid valve, while the left atrium is separated from the left ventricle by the mitral valve. The right and left atriums are separated by the interatrial septum, while the right and left ventricles are separated by the interventricular septum.

Within the heart, the right atrium can generally be accessed from the superior vena cava or the inferior vena cava while the right ventricle is typically accessed from the right atrium. The left ventricle may be accessed from the aorta. The left atrium however, can only be accessed directly from the left ventricle because the pulmonary veins, which are connected to the left atrium are inaccessible. The left ventricle approach to the left atrium is generally considered to be a very difficult procedure because of the tortuous path the catheter must follow. If not correctly performed, this procedure may cause an arrthymia. Therefore, an alternative approach known as a transseptal catheterization was developed to minimize the occurrence of arrthymias. In this procedure, a hole is punctured through the interaatrial septum to gain access to the left atrium of the heart with the use of a needle.

A transeptal needle catheter, generally comprising three separate components, is typically used to perform a transseptal catheterization procedure. These catheter devices are generally composed of a sheath, a dilator and a needle. FIG. 1 illustrates an embodiment of a prior art transseptal needle catheter 10. As shown, the prior art device 10 comprises an outer tubular sheath 12 having an inner sheath lumen that extends longitudinally from a proximal sheath end to a distal sheath end. The outer sheath 12 is connected to a sheath hub 14 at its proximal end. A dilator 16 comprising an elongated tubular body having an outer diameter and an inner dilator lumen, is slidably positioned within the inner lumen of the outer sheath 12. The cross-sectional diameter of the dilator 16 is constructed such that it is narrower than the inner diameter of the lumen of the sheath 12.

A cannula needle 18 is positioned in a slidable relationship within the dilator lumen. The cannula needle 18 comprises an elongated tubular shaped body having a cross-sectional diameter that is smaller than that of the dilator 16. As shown in FIG. 1, the proximal end of the cannula needle 18 is further connected to a needle assembly 20 which provides mechanical support and a means to control the cannula needle 18. An elongated stylet 22 is slidably positioned within the inner diameter of the cannula needle 18.

Thus, the prior art needle catheter 10 is constructed with a series of tubular bodies, the elongated outer sheath 12, the dilator 16, the cannula needle 18 and the stylet 22 that are positioned within one another and are each capable of independent axial movement with respect to each other. FIG. 2 illustrates a magnified cross-sectional view of the distal end of a prior art needle catheter 10 showing the independent slidable relationship between the outer sheath 12, dilator 16, cannula needle 18, and stylet 22.

In a typical transseptal procedure, access to the femoral vein is first gained via the Seldinger technique. The catheter is then positioned within the vasculature of the heart. Second, a guide wire is passed through an introducer sheath and threaded up the inferior vena cava to the superior vena cava. The sheath and dilator assembly are then maneuvered over the guide wire into the superior vena cava. The guide wire is then removed from the catheter. Once the guide wire is removed, the needle assembly is advanced through the inner lumen of the dilator until the distal tip of the stylet is positioned just proximal of the distal end of the dilator. Next, the stylet is removed. The dilator/sheath/needle assembly is then positioned adjacent to the intended position within the heart, more specifically, the septal wall (fossa ovalis). At this point in the procedure, it is critical that the dilator, sheath and needle portions are correctly positioned relative to each other so as not to inadvertently puncture or damage surrounding tissue. The needle portion is then advanced through the dilator to puncture the targeted tissue, i.e., the septal wall. Finally, the sheath and dilator assembly are fed through the septal wall over the needle thereby gaining access to the left atrium.

The present invention, therefore, provides a cost effective needle assembly device having a one-piece assembly cannula construction that fluidly transitions from a larger diameter main portion to a smaller diameter needle portion, at the distal end of the assembly. In addition, the handle of the transseptal needle assembly is designed with an improved ergonomic design having an optimally distributed ballast therewithin. Such an improved ergonomic design and ballast improves the control and tactile feel of the needle assembly by a physician.

SUMMARY OF THE INVENTION

The present invention provides a cost effective needle assembly designed to be used to facilitate various vascular procedures, such as a transseptal catheterization procedure. The needle assembly of the present invention comprises an elongated cannula, a handle, and a stylet. The needle assembly may also comprise a stopcock to control the flow of fluids therewithin. The cannula of the assembly comprises an elongated tubular body having an internal lumen extending lengthwise therewithin. The cannula of the assembly extends distally from within the assembly handle. The cannula of the needle assembly has a uniform body construction from its proximal end to its distal end. In addition, the distal end portion of the cannula is constructed such that the cross-sectional diameter progressively narrows as the cannula extends distally to the end of the assembly. The cannula of the needle assembly of the present invention comprises a needle end portion that fluidly extends distally from the larger diameter main cannula portion at the end of the assembly.

The handle assembly of the needle assembly of the present invention comprises a handle housing constructed of a lightweight durable polymeric material. In addition, the handle assembly comprises a handle sleeve and handle slug that are positioned within the handle housing. The handle sleeve and handle slug, which are preferably composed of a metallic material, anchor the proximal end of the cannula within the handle housing. In addition, the handle sleeve and handle slug provide ballast for the handle. The incorporation of ballast within the handle of the needle assembly provides improved tactile feel and, thus, improved control of the needle end portion of the cannula of the assembly.

The needle assembly of the present invention may further comprise a stopcock that is positioned at the proximal end of the assembly handle. If so attached, the stopcock provides a valve to control the introduction or removal of fluids through the length of the assembly.

In addition, the needle assembly may also comprise a stylet that extends longitudinally through the stopcock and the lumen of the assembly from the proximal end through the distal end. The stylet is designed to extend through the distal end of the needle tip of the assembly and provides a means to minimize inadvertent contact or skiving of the distal end of the needle end within the lumen of the dilator. The proximal end of the stylet comprises a stylet handle having a hinge design that removably secures the stylet to the proximal end of the stopcock or assembly handle housing.

BRIEF DESCRIPTION OF THE DRAWINGS

FIG. 1 is a side view of an embodiment of a dilator hub and needle assembly of a prior art needle catheter.

FIG. 2 is a magnified cross-sectional view of the distal end of the prior art needle catheter shown in FIG. 1.

FIGS. 7 and 8 illustrate side views of an embodiment of the proximal end portion of the needle assembly shown in FIG. 3.

DETAILED DESCRIPTION OF THE PREFERRED EMBODIMENTS

Figure 3:
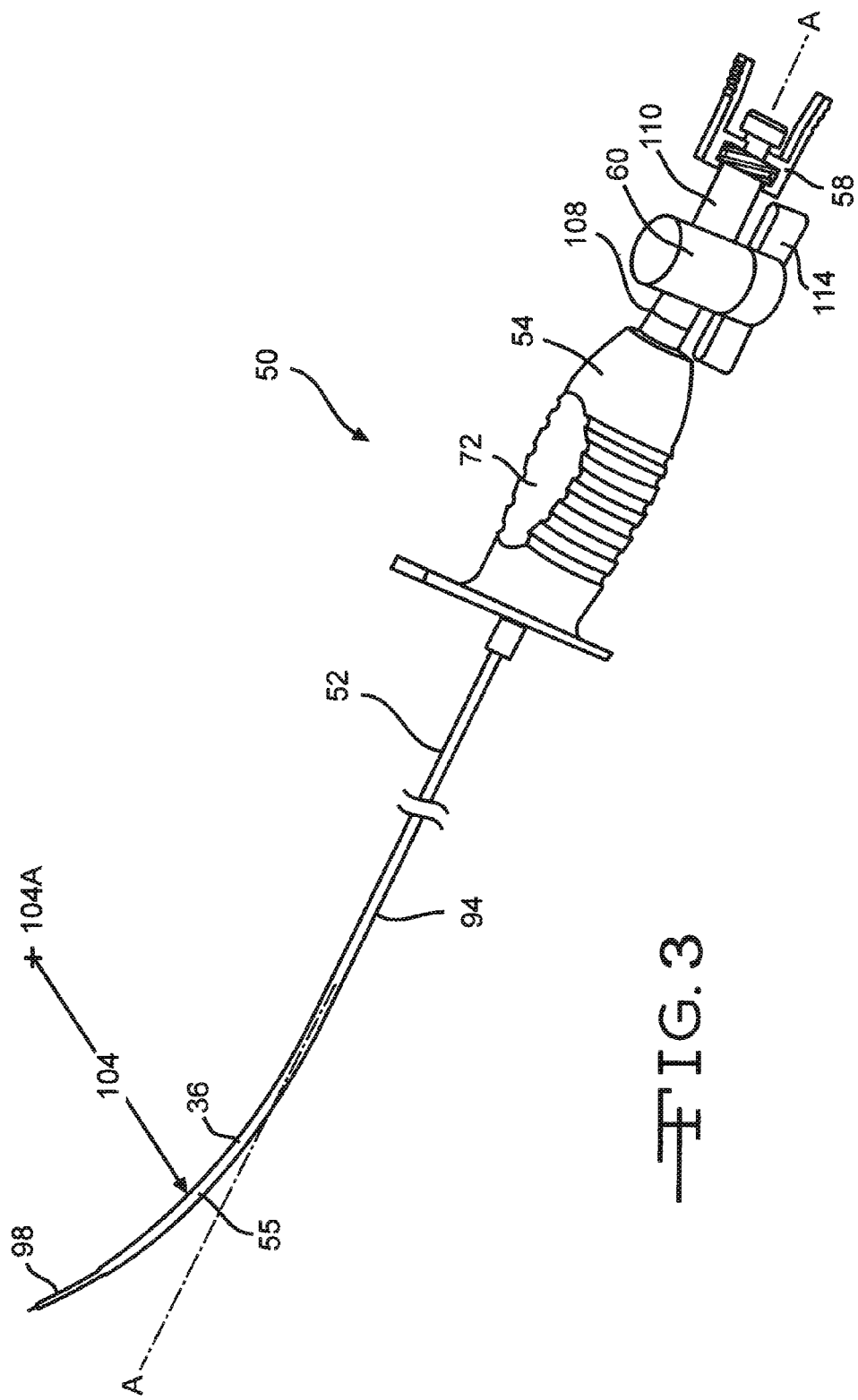
FIG. 3 is a perspective view of an embodiment of a needle assembly of the present invention.

Now turning to the figures, FIGS. 3-8 illustrate embodiments of a transseptal needle assembly 50 of the present invention. As illustrated in FIG. 3, the needle assembly 50 comprises an elongated cannula 52, having a cannula proximal end portion 53 (FIG. 5) spaced from a cannula distal end portion 55. In addition, the needle assembly 50 further comprises a handle 54, a stylet 56, and a stylet handle 58. A stopcock 60 may also be removably attached to the needle assembly 50. As shown the cannula 52 extends distally from the handle 54 while the stopcock 60 and stylet handle 58 are positioned proximally from the assembly handle 54.

Figure 4:
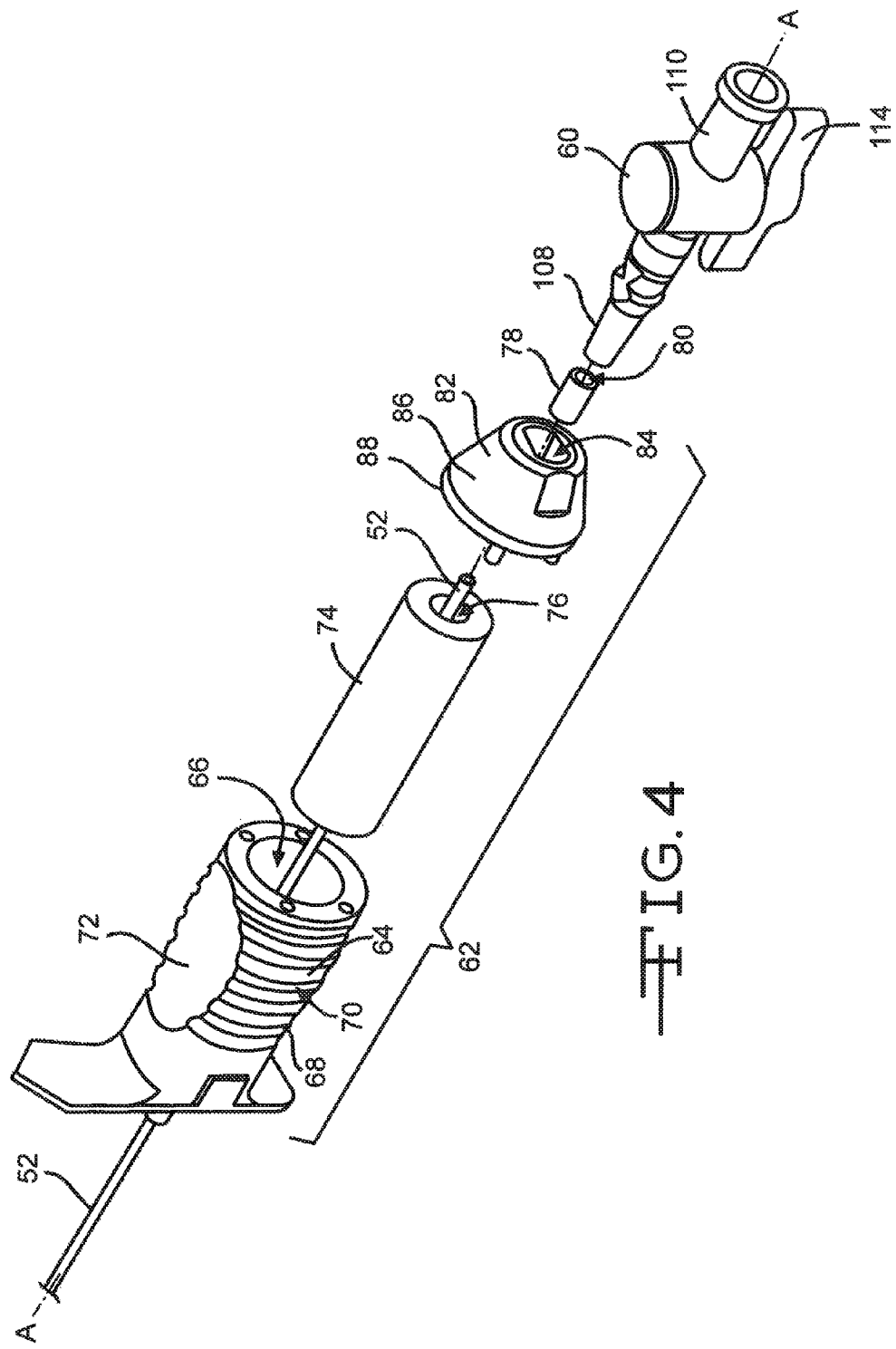
FIG. 4 is an exploded perspective view of an embodiment of the components comprising a handle assembly of the needle assembly shown in FIG. 3.

FIG. 4 shows an exploded view of an embodiment of a handle assembly 62 of the needle assembly 50 of the present invention. As shown, the handle assembly 62 comprises a handle housing 64 having a handle cavity 66 therewithin. In a preferred embodiment, the handle housing 64 has an ergonomic shape. More specifically, the handle 54 comprises a series of ridges 68 that protrude from an exterior surface 70 of the handle housing 64. The ridges 68 are positioned such that they extend circumferentially around the handle housing 64. In addition, at least one depression area 72 is formed within a portion of the exterior surface 70 of the handle housing 64. In a preferred embodiment, the depression area 72 has a curved perimeter, more preferably the depression area 72 has an oval perimeter. The series of handle ridges 68 combined with the depression area 72 provide an improved means with which to grip the needle assembly 50. The depression area 72 provides a thumb rest while the series of ridges 68 provides an exterior handle surface that minimizes slippage of the handle 54 and the needle assembly 50 while performing a catheterization procedure.

Figure 5:
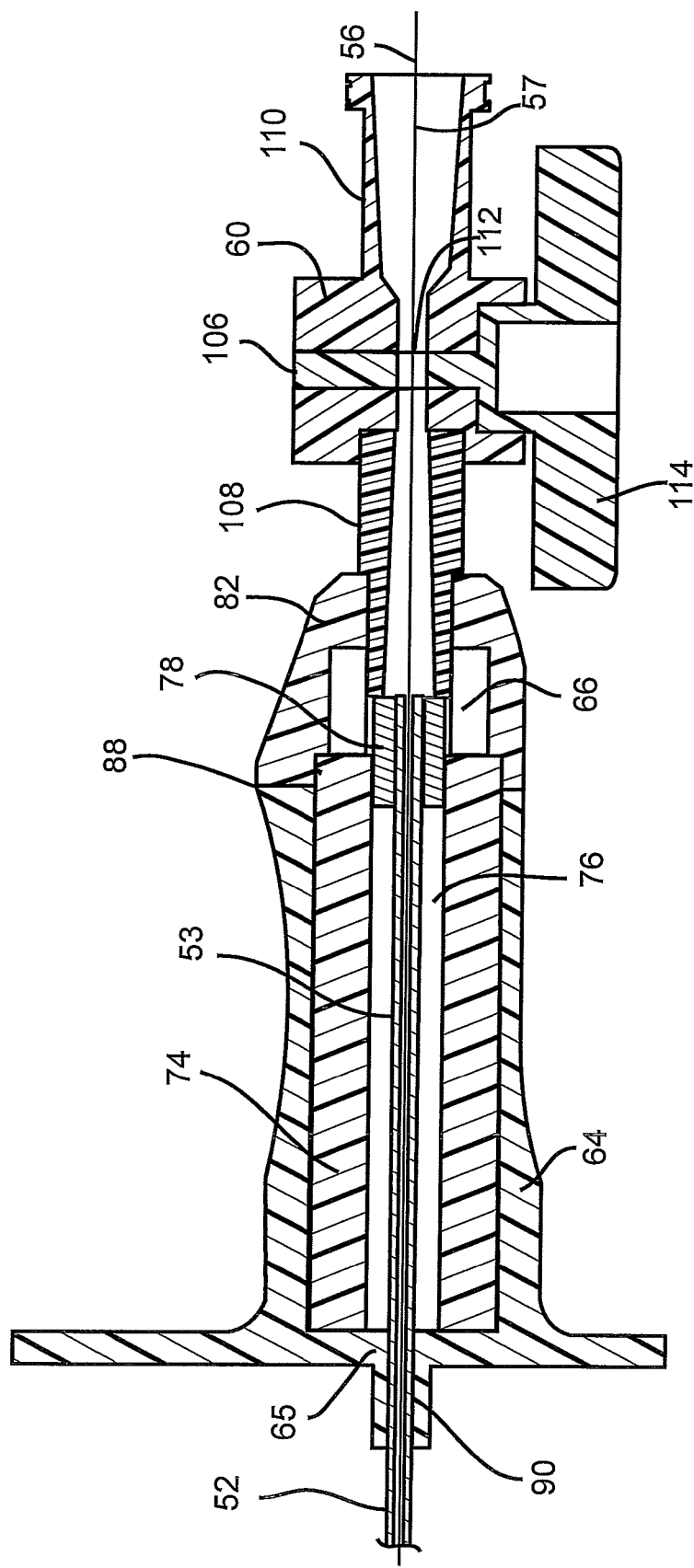
FIG. 5 is a magnified cross-sectional view of an embodiment of the handle and stopcock features comprising the proximal end portion of the needle assembly illustrated in FIG. 3.

A handle sleeve 74, having a tubular body and an inner sleeve lumen 76 extending therewithin, is positioned within the handle cavity 66. The handle sleeve 74 is designed such that the proximal end portion 53 of the cannula 52 extends through the sleeve lumen 76. As shown in FIG. 5, a handle slug 78, comprising a handle slug through-bore 80 (FIG. 4), is further positioned within the lumen 76 of the handle sleeve 74. In an embodiment, the handle slug 78 resides at least partially within the sleeve lumen 76. Alternatively, the slug 78 may be positioned completely within the lumen 76 of the sleeve 74. The handle slug 78 provides mechanical support and anchors the proximal end portion 53 of the cannula 52 within the handle 54. In addition, the handle sleeve 74 and the handle slug 78 provides ballast to the handle assembly 62. Ballast within the handle 54 aids in the puncture of the targeted tissue by affording a physician improved control of the advancement or retraction of the needle assembly 50. The correct amount and position of ballast within the handle 54 provides an improved tactile feel of the movement of the needle assembly 50, particularly of the cannula distal end portion 55. If too much or too little ballast is provided in the handle 54, it may be difficult for a physician to be cognizant of the tactile feedback from the needle assembly 50. As a result, the distal end of the cannula 52 may be inadvertently advanced through vascular tissue. In a preferred embodiment, the weight of the handle sleeve 74 ranges from about 15 to 25 grams. In addition, the handle slug 78 may be positioned within at least a portion of the proximal end portion of the handle sleeve 74.

In a preferred embodiment, the handle housing 64 is composed of a polymeric material such as polyvinyl chloride (PVC), polyvinyl butyral (PVB), or an acrylic material. The handle sleeve 74 and handle slug 78 may be composed of a metallic material such as stainless steel, for example, stainless steel 304, titanium or MP35N.

As shown in FIGS. 4 and 5, a handle end cap 82 is positioned at the proximal end of the handle 54. A handle end cap through-bore 84 extends though the proximal end of the end cap 84. The end cap through-bore 84 provides an opening through which the stopcock 60 may be positioned and the stylet 56 can advance therethrough. In a preferred embodiment, the handle end cap 84 comprises a frustoconical construction, having an end cap sidewall 86 that extends proximally and inwardly toward a longitudinal axis A-A from an end cap base 88. The end cap base 88 is preferably positioned and attached at the proximal end of the handle housing 64. In a preferred embodiment as illustrated in FIGS. 3 and 4, the components of the handle assembly 62 and stopcock 60 are positioned about co-axial along the longitudinal axis A-A. Like the handle housing 64, the handle end cap 82 may be composed of a polymeric material such as, but not limited to, polyvinyl chloride (PVC), polyvinyl butyral (PVB), polycarbonate, or an acrylic material.

As shown in FIGS. 3-5, the proximal end portion 53 of the cannula 52 is positioned within the handle assembly 62. Specifically as shown in the cross-sectional view of FIG. 5, the proximal end of the cannula 52 is positioned within the lumen 76 of the handle sleeve 74. The proximal end portion 53 of the cannula 52 is preferably positioned through a handle housing throughbore 90 located at the distal end of the handle housing 64. The distal throughbore 90 is in open communication with the handle cavity 66.

Figure 6:
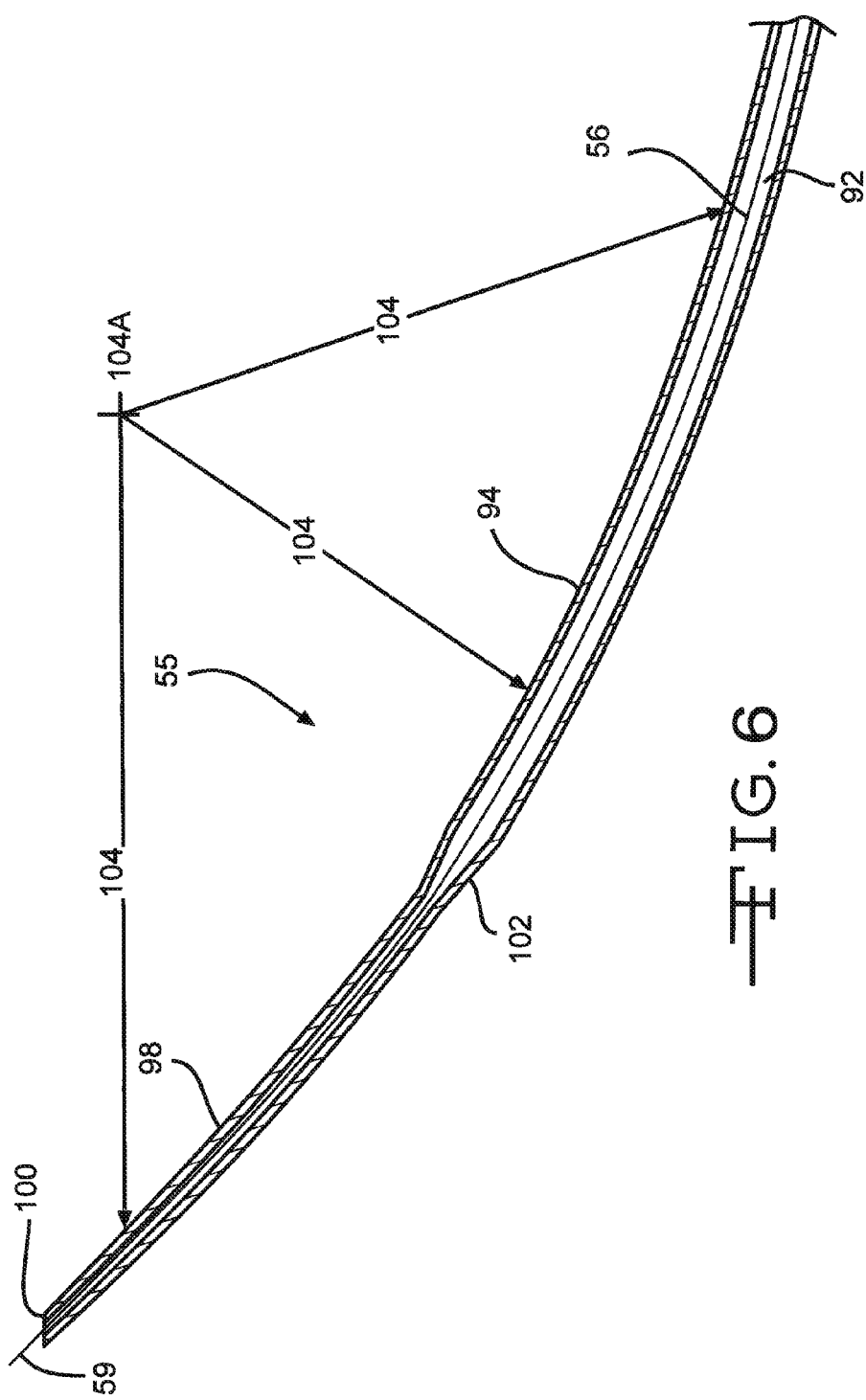
FIG. 6 is a magnified cross-sectional view of the distal end portion of the cannula comprising the needle assembly of the present invention.

As previously mentioned, the cannula 52 extends distally from the handle housing 64 (FIGS. 3-5). In a preferred embodiment, the cannula 52 comprises a "one-piece" construction having an inner cannula lumen 92 (FIG. 6) that extends the entire length of the cannula 52. The lumen 92 thus enables the stylet 56 to extend through the cannula 52 from its proximal end to the distal cannula end. The assembly cannula 52 has a uni-body "one piece" construction comprising a main cannula portion 94 and a needle portion 98. As the cannula 52 extends distally from the handle housing 64, the cannula 52 fluidly transitions from the main cannula portion 94 to the needle portion 98. The main cannula portion 94 has a preferably uniform outer diameter that extends from within the handle housing 64. As illustrated in FIG. 6, the distal portion 55 of the cannula 52 of the needle assembly 50 of the present invention comprises the needle portion 98.

In a preferred embodiment, the main cannula portion 94 has a main cannula length that ranges from about 25 cm to about 130 cm. The needle portion 98 of the assembly 50, located at the distal end of the cannula 52, fluidly extends from the main cannula portion 94. In a preferred embodiment, the needle portion 98 has a needle portion length that ranges from about 0.5 cm to about 8 cm. In a preferred embodiment, the needle portion 98 comprises a beveled needle tip 100 residing at the distal end of the needle assembly 50. The beveled needle tip 100 provides an angled sharp cutting surface with which to cut tissue.

As illustrated in FIG. 6, the cannula 52 may comprise a taper portion 102 having a frusto-conical shape extending distally and inwardly toward an imaginary centerline of the lumen 92 as it transitions the main cannula portion 94 to the smaller diameter needle portion 98. With respect to the embodiment illustrated in FIGS. 5 and 6, the imaginary centerline of lumen 92 resides approximately along stylet 56. As the cannula 52 transitions to the distal end, the outer diameter becomes progressively smaller. In a preferred embodiment, the main cannula portion 94 has a main cannula cross-sectional diameter that ranges from about 0.10 cm to about 0.50 cm. The needle portion 98 has a needle cross-sectional diameter that ranges from about 0.05 cm to about 0.10 cm. The inner cannula lumen 92 that extends within the entire length of the cannula 52 has a cross-sectional diameter that is less than about 0.10 cm. In a preferred embodiment, the inner cannula lumen 92 has a cross-sectional diameter that ranges from about 0.01 cm to about 0.1 cm.

In a preferred embodiment, the cannula 52 of the needle assembly 50 is composed of a metallic material. Specifically, the cannula 52 may be composed of stainless steel, particularly stainless steel 304. In addition, the cannula 52 may be composed of other metallic materials such as, but not limited to, titanium, MP35N, platinum, palladium, niobium, combinations thereof and alloys thereof.

The cannula 52 is designed to be flexible and may have a curved orientation. The general flexible nature of the cannula 52 enables it to advance within the tortuous paths of the vasculature. In an embodiment, the orientation of the distal end portion 55 of the cannula 52 may deviate from longitudinal axis A-A. More specifically, as shown in FIG. 3, the distal portion 55 of the cannula 52 of the needle assembly 50 may have a curved presentation. Specifically, the distal portion 55 of the cannula 52 may have a cannula radius of curvature 104 ranging from about 2 inches to about 20 inches from an imaginary focal point 104A.

In the embodiment illustrated in FIGS. 3, 4, 7, and 8 the stopcock 60 is positioned at the proximal end of the handle housing 64. The stopcock 60 provides a means of controlling the flow of fluids from within and out of the needle assembly 50. In a preferred embodiment, the stopcock 60 comprises a valve portion 106 (FIG. 5), a luer fitting 108, and at least one inlet portion 110. The stopcock valve 106 is preferably positioned between the luer fitting 108 and the inlet portion 110.

In a preferred embodiment, the valve portion 106 comprises a rotatable cylinder 106 having a series of openings 112 therethrough. The openings 112 are preferably positioned such that fluid flow can be controlled with the turn of a valve handle 114. In a preferred embodiment, the valve handle 114 is connected to the valve 106 within the stopcock 60 such that the flow of fluids can be turned on and off with rotational movement of the cylinder 106.

As shown in FIGS. 7 and 8, the luer fitting 108 and the stopcock inlet 110 are preferably aligned along longitudinal axis A-A. However, additional valve inlets 110 may be connected to the stopcock 60. These additional inlets 110 enable the controlled flow of additional fluids through the assembly 50. In a preferred embodiment, the luer fitting 108 is removably positioned within the proximal end of the handle housing 64. Thus, the stopcock 60 may be removed from the assembly 50 if desired.

As illustrated in FIGS. 3, 7 and 8, the stylet 56 has a stylet proximal end portion 57 (FIG. 5) spaced from a stylet distal end portion 59 (FIG. 6). The stylet 56 is preferably positioned through the proximal end of the inlet 110 of the stopcock 60, such that the stylet distal end portion 59 is advanced through the needle assembly 50. The stylet 56 is preferably advanced through one of the valve openings 112 of the stopcock 60 such that the stylet 56 is allowed to reach the distal end of the needle assembly 50. Alternatively, if the stopcock 60 is not present, the stylet 56 may be positioned directly through the proximal end of the inlet 110 of the luer fitting 108.

As shown, the proximal end portion 57 of the stylet 56 is connected to the stylet handle 58. In a preferred embodiment, the stylet handle 58 is of a hinged designed having opposed lever arms 116. More specifically, the stylet handle 58 comprises two opposing lever arms 116 that are connected to a stylet handle knob 118. Each of the opposing lever arms 116 comprises a support member 120 that extends in an inwardly arched or curved manner from an opposing exterior surface of each of the lever arms 116. In the locked position of the stylet handle 58 shown in FIG. 7, the opposing exterior surfaces of the lever arms 116 are orientated about parallel to longitudinal axis A-A.

As shown in FIGS. 7 and 8, the support members 120, of the respective opposing lever arms 116, are joined to the stylet handle knob 118. More specifically, each of the support members 120 is joined to a knob extension member 122 that protrudes distally from the stylet handle knob 118. In addition to the respective support members 120, each lever arm 116 comprises a lip portion 124 that extends about perpendicular from an exterior surface at the distal end of the arm 116. The lip portion 124 and the support member 120 are spaced apart such that an end portion 126 of the stopcock inlet 110 fits therewithin. Although not preferred, the transseptal needle assembly 50 of the present invention may be constructed without a stopcock 60. In this case, an end portion of the luer inlet is attached to the proximal end of the stylet handle 58.

As illustrated in FIGS. 7 and 8, the stylet handle 58 provides a means to removably fixate the stylet 56 within the cannula lumen 76. As shown, the support members 120 and opposing lever arms 116 are oriented in a pivotable relationship such that a hinge mechanism is created. As illustrated in FIG. 8, as the proximal ends of the lever arms 116 are brought closer together, the respective distal ends of the lever arms 116 and the lip portions 124 are positioned away from each other. When fully extended, the lip portions 124 are no longer in contact with the proximal end of the stopcock inlet 110. Thus, the stylet 56 may be moved in a proximal or distal direction within the assembly 50.

In a preferred embodiment, the stylet 56 may comprise a flexible guide wire having a diameter ranging from about 0.01 cm to about 0.1 cm. Alternatively, the stylet 56 may comprise a rod having an outer diameter ranging from about 0.1 cm to about 1 cm. In either case, the outer diameter of the stylet 56 should be less than the diameter of the inner lumen 92 of the cannula 52 such that the stylet 56 may be unobstructively advanced therethrough. In a preferred embodiment, the stylet 56 is composed of a metallic material. More specifically, the stylet 56 may be composed of a metallic material such as MP35N, titanium, stainless steel, platinum, palladium, niobium, combinations thereof and alloys thereof.

In addition, the present invention provides an efficient and cost effective method of manufacture. In a first step, the handle housing 64 and the handle end cap 82 are fabricated using a molding technique. In a preferred embodiment, injection molding is used to fabricate the handle housing 64 and the handle end cap 82 portions.

Next, the elongated cannula 52, housing sleeve 74 and housing slug 78 are fabricated to the desired length and cross-sectional diameter dimensions. Once the cannula 52 and housing slug 78 are fabricated, the handle slug 78 is positioned and adhered around an external surface of the proximal end portion of the cannula 52. In an embodiment, the cannula 52 is advanced through the slug through-bore 80 such that the slug 78 extends circumferentially around the proximal end portion of the cannula 52. In a preferred embodiment, the handle slug 78 is adhered to the exterior surface of the cannula 52 through the use of an ultra violet (UV) light curing adhesive.

After the cannula 52 and handle slug 78 sub-assembly has been prepared, the handle sleeve 74 is positioned within the housing cavity 66. The distal end of the cannula 52 is then threaded through the handle 52 such that the handle slug 78 is positioned at least partially within the handle sleeve 74 (FIG. 5). Once the slug 78 and cannula 52 sub-assembly is positioned within the handle sleeve 74, the housing end cap 82 is adhered to the proximal end of the handle housing 64, encasing the sleeve 75 and handle slug 78 therewithin. In a preferred embodiment, a UV light curing adhesive may be used to adhere the handle end cap 82 to the proximal end of the handle housing 64. If desired, the stopcock 60 may be positioned and adhered to the proximal end of the housing end cap 82.

In an alternate, after the cannula 52 and handle slug 78 sub-assembly has been prepared, the distal end of the cannula 52 is threaded through the luer fitting 108 thus positing the handle slug 78 within a distal end portion of the luer fitting 108 of the stopcock 60. Once the handle slug 78 is positioned within the luer fitting, the slug 78 is then adhered therewithin. In a preferred embodiment, a UV curing material may be used to adhere the handle slug 78 within the luer fitting 108. The stopcock 60 may then be joined and adhered to the proximal end of the luer fitting 108. A UV curing material may be used to join the stopcock 60 to the proximal end of the luer fitting 108.

The housing end cap 82 is then adhered to the distal end of the luer fitting 108 (FIG. 5). In a preferred embodiment, the distal end of the cannula 52 is threaded through the handle end cap through-bore opening 84. A UV light curing material may also be used to adhere the handle end cap 82 to the luer fitting 108. After the housing end cap 82 is adhered to the luer fitting 108, the distal end of the cannula 52 is threaded through the handle housing throughbore 90 and the handle housing 64 is advanced over the cannula 52. In an embodiment, the handle sleeve 74 may be advanced over the cannula 52 prior to advancing the distal end of the cannula 52 through the handle housing throughbore 90 or alternately, the handle sleeve 74 may be positioned within the handle housing cavity 66 prior to advancing the cannula 52 through handle housing 64. The handle end cap 82 is then adhered to the proximal end of the handle housing 64, thereby encasing the handle sleeve 74 therewithin. In a preferred embodiment, a UV light curing material is used to join the handle housing end cap 82 to that of the proximal end of the handle housing 64. In either embodiment, it is preferred that the handle sleeve 74 remains free floating within the handle cavity 66.

In operation, access within the femoral vein is first gained via the Seldinger technique. Once the introducer sheath is correctly positioned within the femoral vein, a guide wire is advanced through the introducer sheath and threaded up the inferior vena cava to the superior vena cava. A sheath and dilator assembly is then advanced over the guide wire into the superior vena cava. The guide wire is then removed. Once the guide wire is removed, the cannula 52 of the needle assembly 50 of the present invention is advanced through the lumen of the dilator until the distal end 59 of the stylet 56 is positioned just proximal of the distal end of the dilator. The stylet 56 is then removed from the needle assembly 50. After the stylet 56 has been removed, the needle tip 100 of the cannula 52 is advanced through the vasculature tissue, particularly a septal wall, creating a hole therethrough.

After the septum has been punctured, fluids such as saline and/or medications may be introduced within the vasculature through the stopcock 60. Likewise, suction may be applied at the inlet opening 110 of the stopcock 60 to remove fluids from the targeted vasculature area. Once the needle portion 98 has been advanced through the vasculature tissue such as the septal wall, the dilator and/or sheath assemblies of the needle catheter may be advanced over the needle portion 98 and through the hole thereby gaining access to the left atrium. If desired, fluids may be introduced or removed from within the vasculature through the stopcock 60.

Now, it is therefore apparent that the present invention has many features and benefits among which are providing a cost effective transseptal needle assembly 50. The transseptal needle assembly 50 further comprising an ergonomic handle assembly with a ballast that provides optimal tactile feedback. While embodiments of the present invention have been described and illustrated in detail, they are for the purpose of illustration, not limitation.

What is claimed is:

1. A transseptal needle assembly, comprising:
   a) an assembly handle, comprising:
      i) a housing having a housing sidewall comprising an inner housing surface defining a housing lumen extending along a longitudinal axis from a proximal housing end wall at a proximal housing open end to a distal housing open end;
      ii) a sleeve comprising a sleeve sidewall having an inner sleeve surface defining a sleeve lumen extending along the longitudinal axis from a proximal sleeve open end to a distal sleeve open end, wherein the sleeve is received in the housing lumen;
      iii) a slug comprising a slug sidewall having an inner slug surface defining a slug lumen extending from a proximal slug open end to a distal slug open end, wherein the slug is received in the sleeve lumen with the proximal slug open end adjacent to the proximal sleeve open end; and
      iv) an end cap comprising a cap sidewall having an inner cap surface defining a cap lumen extending for a cap length from a proximal cap open end to a distal cap end wall at a distal cap open end; and
   b) an elongated cannula comprising a cannula sidewall having an inner cannula surface defining a cannula lumen extending from a distal cannula portion having a distal cannula open end to a proximal cannula portion having a proximal cannula open end,
   c) wherein:
      i) the proximal cannula portion is received in the slug lumen,
      ii) the slug is received in the sleeve lumen, and
      iii) the sleeve is received in the housing lumen, and
   d) wherein the distal cannula portion having the distal cannula open end extends distally from the assembly handle, and
   e) wherein with the proximal cannula portion received in the slug lumen of the slug received in the sleeve, in turn, received in the housing, the distal cap end wall contacts the proximal housing end wall to thereby fixedly house the proximal cannula end inside the assembly handle.

2. The transseptal needle assembly of claim 1 wherein the cannula sidewall tapers from a first, greater diameter at the proximal cannula portion to a second, lesser diameter at the distal cannula open end.

3. The transseptal needle assembly of claim 1 further comprising a stylet having a proximal stylet end connected to a stylet handle detachably connected to the assembly handle.

4. The transseptal needle assembly of claim 3 wherein the stylet handle comprises opposing lever arms connected in a hinged relationship to a stylet knob, and wherein the opposing lever arms are manipulatable to connect and disconnect the stylet to and from the assembly handle.

5. The transseptal needle assembly of claim 1 wherein the cannula distal portion is manipulatable into a curved shape having a radius of curvature ranging from about 2 inches to about 20 inches with respect to the longitudinal axis.

6. The transseptal needle assembly of claim 1 wherein a luer fitting of a stop cock is received in the proximal cap open end, the stop cock being in open communication with the cannula lumen.

7. The transseptal needle assembly of claim 1 wherein the slug is composed of a material selected from the group consisting of stainless steel, titanium, MP35N, platinum, palladium, niobium, and alloys thereof.

8. The transseptal needle assembly of claim 1 wherein the sleeve has a weight ranging from about 15 grams to about 25 grams.

9. The transseptal needle assembly of claim 2 wherein the second, lesser diameter portion of the cannula has a cross-sectional diameter ranging from about 0.05 cm to about 0.10 cm.

10. The transseptal needle assembly of claim 1 wherein the cannula forms a needle at the distal cannula open end.

11. The transseptal needle assembly of claim 1 wherein the housing and end cap are composed of a material selected from the group consisting of polyvinyl chloride (PVC), polyvinyl butyral (PVB), and an acrylic material.

12. The transseptal needle assembly of claim 1 wherein an intermediate cannula portion between the proximal and distal cannula open ends contacts the inner housing surface at the distal housing open end.

13. The transseptal needle assembly of claim 1 wherein, with the sleeve received in the housing lumen, the proximal slug open end extends proximally out past the proximal sleeve open end.

14. The transseptal needle assembly of claim 1 wherein, with the sleeve received in the housing lumen, the proximal sleeve open end extends proximally out past the proximal housing open end.

15. The transseptal needle assembly of claim 1 wherein the cannula is composed of a material selected from the group consisting of stainless steel, titanium, MP35N, platinum, palladium, niobium, and alloys thereof.

16. The transseptal needle assembly of claim 1 wherein a series of ridges protrude circumferentially from an exterior surface of the housing sidewall.

17. The transseptal needle assembly of claim 1 wherein the housing sidewall comprises at least one depression area.

18. A transseptal needle assembly, comprising:
   a) an assembly handle, comprising:
      i) a housing having a housing sidewall comprising an inner housing surface defining a housing lumen extending along a longitudinal axis from a proximal housing end wall at a proximal housing open end to a distal housing open end;
      ii) a sleeve comprising a sleeve sidewall having an inner sleeve surface defining a sleeve lumen extending along the longitudinal axis from a proximal sleeve open end to a distal sleeve open end, wherein the sleeve is received in the housing lumen;
      iii) a slug comprising a slug sidewall having an inner slug surface defining a slug lumen extending from a proximal slug open end to a distal slug open end, wherein the slug is received in the sleeve lumen with the proximal slug open end adjacent to the proximal sleeve open end; and
      iv) an end cap comprising a cap sidewall having an inner cap surface defining a cap lumen extending for a cap length from a proximal cap open end to a distal cap end wall at a distal cap open end;
   b) an elongated cannula comprising a cannula sidewall having an inner cannula surface defining a cannula lumen extending from a distal cannula portion having a distal cannula open end to a proximal cannula portion having a proximal cannula open end, c) wherein:
  i) the proximal cannula portion is received in the slug lumen,
  ii) the slug is received in the sleeve lumen, and
  iii) the sleeve is received in the housing lumen, and d) wherein the distal cannula portion having the distal cannula open end extends distally from the assembly handle, and e) wherein with the proximal cannula portion received in the slug lumen of the slug received in the sleeve, in turn, received in the housing, the distal cap end wall contacts the proximal housing end wall to thereby fixedly house the proximal cannula end inside the assembly handle;

f) a stop cock comprising a luer fitting received in the proximal cap open end, wherein the stop cock including the luer fitting is in open communication with the cannula proximal open end received in the slug, and wherein a proximal stop cock end has a first outer diameter extending distally to a second outer diameter less than the first outer diameter; and g) a stylet extending from a proximal stylet end at a stylet handle to a distal stylet end, wherein the stylet handle resides proximal the stop cock with the stylet being movably received in the cannula, and wherein the stylet handle has opposing lever arms connected in a hinged relationship by respective support members to a centrally located stylet knob, h) wherein with the stylet handle removably connected to the stop cock, the opposing lever arms are manipulatable into an open position spaced further apart than the first outer diameter of the proximal stop cock end so that the stylet handle is axially manipulatable:
  i) in a proximal direction away from the stop cock to move the distal stylet end proximally inside the cannula; and
  ii) in a distal direction toward the stop cock to thereby cause the distal stylet end to move distally inside the cannula with the opposing lever arms being further manipulatable into a closed position to removably contact the stop cock where the first outer diameter meets the second, lesser outer diameter to thereby fix the stylet with respect to the cannula lumen.

19. The transseptal needle assembly of claim 18 wherein each lever arm of the stylet handle comprises a distal lip portion extending inwardly toward the longitudinal axis so that with the stylet handle in the closed position, the distal lip portions of the lever arms removably contact the proximal stop cock end.

20. The transseptal needle assembly of claim 18 wherein the cannula sidewall tapers from a third, greater diameter to a fourth, lesser diameter at the distal cannula open end.

21. The transseptal needle assembly of claim 18 wherein the slug is composed of a material selected from the group consisting of stainless steel, titanium, MP35N, platinum, palladium, niobium, and alloys thereof.

22. The transseptal needle assembly of claim 18 wherein the housing and end cap are composed of a material selected from the group consisting of polyvinyl chloride (PVC), polyvinyl butyral (PVB), and an acrylic material.

23. The transseptal needle assembly of claim 18 wherein the cannula is composed of a material selected from the group consisting of stainless steel, titanium, MP35N, platinum, palladium, niobium, and alloys thereof.

24. The transseptal needle assembly of claim 18 wherein the proximal slug open end extends proximally out past the proximal sleeve open end inside the housing.

25. The transseptal needle assembly of claim 18 wherein the proximal sleeve open end extends proximally out past the proximal housing open end inside the housing.

26. A transseptal needle assembly, comprising:
  a) an assembly handle, comprising:
    i) a housing having a housing sidewall comprising an inner housing surface defining a housing lumen extending along a longitudinal axis from a proximal housing end wall at a proximal housing open end to a distal housing open end, wherein the housing lumen has a proximal housing lumen portion of a first, greater diameter extending distally from the proximal housing open end partway along the housing length to a distal housing lumen portion of a second, lesser diameter extending distally the remainder of the housing length to the distal housing open end;
    ii) a sleeve comprising a sleeve sidewall having an inner sleeve surface defining a sleeve lumen extending along the longitudinal axis from a proximal sleeve open end to a distal sleeve open end, wherein the sleeve is received in the housing lumen with the distal sleeve open end contacting the housing where the proximal housing lumen portion of the first, greater diameter meets the distal housing lumen portion of the second, lesser diameter, and wherein the proximal sleeve open end is disposed adjacent to the proximal housing open end;
    iii) a slug comprising a slug sidewall having an inner slug surface defining a slug lumen extending from a proximal slug open end to a distal slug open end, wherein the slug is received in the sleeve lumen with the proximal slug open end adjacent to the proximal sleeve open end; and
    iv) an end cap comprising a cap sidewall having an inner cap surface defining a cap lumen extending for a cap length from a proximal cap open end to a distal cap open end, wherein the cap lumen has a proximal cap lumen portion of a third diameter extending distally from the proximal cap open end partway along the cap length to an intermediate cap lumen portion of a fourth diameter extending distally to a distal cap lumen portion of a fifth diameter extending distally the remainder of the cap length to the distal cap open end, and wherein the third diameter is less than the fourth diameter of the intermediate cap lumen portion which, in turn, is less than the fifth diameter of the distal cap lumen portion;
  b) an elongated cannula comprising a cannula sidewall having an inner cannula surface defining a cannula lumen extending from a distal cannula portion having a distal cannula open end to a proximal cannula portion having a proximal cannula open end,
  c) wherein:
    i) the proximal cannula portion is received in the slug lumen,
    ii) the slug is received in the sleeve lumen, and
    iii) the sleeve is received in the housing lumen,
  d) wherein the distal cannula portion having the distal cannula open end extends distally from the assembly handle,
  e) wherein with the proximal cannula portion received in the slug lumen of the slug received in the sleeve, in turn, received in the housing, the distal cap end wall contacts the proximal housing end wall to thereby fixedly house the proximal cannula end inside the assembly handle, and wherein the end cap has a surface where the intermediate cap lumen portion of the fourth diameter meets the distal cap lumen portion of the fifth diameter that contacts the sleeve adjacent to the proximal sleeve open end;

f) a stop cock comprising a luer fitting received in the proximal cap open end, wherein the stop cock including the luer fitting is in open communication with the cannula proximal open end received in the slug, and wherein a proximal stop cock end has a first outer diameter extending distally to a second outer diameter less than the first outer diameter; and g) a stylet extending from a distal stylet end to a proximal stylet end connected to a stylet handle, wherein the stylet handle resides proximal the end cap with the stylet being movably received in the cannula, and wherein the stylet handle is axially manipulatable to move the distal stylet end inside the cannula.

27. The transseptal needle assembly of claim 26 wherein the proximal open slug end extends proximally out past the proximal open sleeve end inside the housing.

28. The transseptal needle assembly of claim 26 wherein the proximal open sleeve end extends proximally out past the proximal open housing end inside the housing.

* * * * *